US010578595B2

(12) United States Patent
Schulz et al.

(10) Patent No.: US 10,578,595 B2
(45) Date of Patent: Mar. 3, 2020

(54) METHOD AND DEVICE FOR THE OPTICAL SCANNING OF A CHROMATOGRAPHIC SAMPLE

(71) Applicant: Merck Patent GmbH, Darmstadt (DE)

(72) Inventors: Michael Schulz, Darmstadt (DE); Michaela Oberle, Rodgau (DE); Thomas Ingendoh, Wuppertal (DE)

(73) Assignee: Merck Patent GmbH, Darmstadt (DE)

( * ) Notice: Subject to any disclaimer, the term of this patent is extended or adjusted under 35 U.S.C. 154(b) by 30 days.

(21) Appl. No.: 15/536,679

(22) PCT Filed: Nov. 20, 2015

(86) PCT No.: PCT/EP2015/002336
§ 371 (c)(1),
(2) Date: Jun. 16, 2017

(87) PCT Pub. No.: WO2016/096078
PCT Pub. Date: Jun. 23, 2016

(65) Prior Publication Data
US 2017/0336371 A1    Nov. 23, 2017

(30) Foreign Application Priority Data

Dec. 19, 2014  (EP) ..................................... 14004313
Mar. 26, 2015  (EP) ..................................... 15000889

(51) Int. Cl.
*G01N 30/95* (2006.01)
*G02B 21/26* (2006.01)
(Continued)

(52) U.S. Cl.
CPC ......... *G01N 30/95* (2013.01); *G01N 21/3151* (2013.01); *G01N 21/5911* (2013.01);
(Continued)

(58) Field of Classification Search
CPC ... G01N 2021/1774; G01N 2021/3155; G01N 21/3151; G01N 21/5911; G01N 2201/101;
(Continued)

(56) References Cited

U.S. PATENT DOCUMENTS 6,096,205 A   8/2000  Haas
6,130,440 A  10/2000  Ogura
(Continued)

FOREIGN PATENT DOCUMENTS

CN   2884737 Y    3/2007
DE   69910065 T2  4/2004
(Continued)

OTHER PUBLICATIONS

International Search Report PCT/EP2015/002336 dated May 2, 2016.
(Continued)

*Primary Examiner* — Kara E. Geisel
*Assistant Examiner* — Amanda Merlino
(74) *Attorney, Agent, or Firm* — Millen White Zelano and Branigan, PC; Csaba Henter (57) ABSTRACT

A method and device for the optical scanning of a chromatographic sample (3), where a sample plate (2) holding the sample (3) is illuminated with light from a first illumination device (13) and the light emitted by the sample plate (2) is detected by an optical detector device (15) which detects in cell form or area form, a second illumination device (14) is preferably firstly activated in a preparation step. The sample plate (2) is displaced in a first displacement direction relative to the detector device (15), illuminated by the first illumination device (13) and a first measurement image is recorded. The sample plate (2) is displaced in a second displacement direction relative to the detector device (Continued)

(15), illuminated by the second illumination device (14), and a second measurement image is recorded.

20 Claims, 2 Drawing Sheets

(51) Int. Cl.
*G01N 21/59* (2006.01)
*G01N 21/31* (2006.01)
*G02B 21/00* (2006.01)
*G02B 21/06* (2006.01)
*G02B 21/36* (2006.01)

(52) U.S. Cl.
CPC .......... *G02B 21/002* (2013.01); *G02B 21/06* (2013.01); *G02B 21/26* (2013.01); *G02B 21/361* (2013.01); *G01N 2021/3155* (2013.01); *G01N 2201/101* (2013.01)

(58) Field of Classification Search
CPC ...... G01N 30/95; G02B 21/002; G02B 21/06; G02B 21/26; G02B 21/361; H04N 1/024; H04N 1/0281; H04N 1/02845; H04N 1/02895; H04N 1/04
See application file for complete search history.

(56) References Cited

U.S. PATENT DOCUMENTS

| | | | |
|---|---|---|---|
| 6,485,687 B1 * | 11/2002 | Spangenberg | G01N 30/95 422/70 |
| 7,015,486 B1 | 3/2006 | Sarbach et al. | |
| 2014/0154792 A1 | 6/2014 | Moynihan | |

FOREIGN PATENT DOCUMENTS

| | | | |
|---|---|---|---|
| JP | 10213865 A | 8/1998 | |
| JP | 2002543632 A | 12/2002 | |
| JP | 2013224901 A | 10/2013 | |
| WO | 2000040957 A1 | 7/2000 | |
| WO | 2006108137 A2 | 10/2006 | |
| WO | WO-2015017046 A1 * | 2/2015 | ............. G01N 33/50 |

OTHER PUBLICATIONS

English machine translation of CN2884737Y published Mar. 28, 2007.

Office Action in corresponding JP Application No. 2017-532774 dated Sep. 10, 2019 (pp. 1-20).

* cited by examiner

METHOD AND DEVICE FOR THE OPTICAL SCANNING OF A CHROMATOGRAPHIC SAMPLE

The invention relates to a method for the optical scanning of a sample, preferably a chromatographic sample, where a sample plate holding the sample is illuminated with light from a first illumination device, and the light emitted by the sample plate is detected by an optical detector device which reads line by line or field by field.

Thin-layer chromatography is an analytical method by means of which individual substances and the composition of samples can be investigated. The sample to be investigated is dissolved in a solvent and typically applied in spot or line form to a thin layer of a suitable, very finely particulate material, such as, for example, silica gel or cellulose. The material layer referred to as stationary phase or separating layer has itself been applied as uniformly as possible to a plate, usually a carrier plate or carrier film or foil made from plastic, aluminium, metal or glass. The coated plate is also referred to as sample plate or TLC plate. A plurality of different samples are often arranged alongside one another on a sample plate. After the application of the samples to be measured, one edge of the sample plate is dipped into a suitable eluent or wetted therewith. Examples of eluents which can be used, depending on the respective sample and the separating-layer material, are nonpolar organic solvents or alternatively polar solvents, or mixtures thereof. The eluent moves through the fine-pored carrier material owing to capillary forces, where the substances present in a sample move with it at different speeds depending on the substance and are thus spatially separated in the direction of movement of the eluent and thus produce a sample track. By means of evaluation, in most cases optical, of the sample fractions which have been spatially separated in the direction of movement of the eluent, individual substances can be identified by comparison with reference samples and possibly also evaluated quantitatively.

Chromatographic evaluation of a sample plate can be carried out using densitometers which have been optimised for such evaluations, which are also known as "TLC scanners". The samples arranged on a sample plate and separated chromatographically are illuminated successively line by line using a dot- or line-form light spot, or scanned, and the light emitted by the sample plate is detected using a densitometer. The illumination of the sample plates can be carried out using light having various wavelengths or wavelength ranges, where, besides illumination with visible light, use is made, in particular, of illumination with UV light. UV absorption measurements or luminescence light measurements can also be carried out in order to obtain additional information on the substances present in the sample.

The commercially available densitometers usually used enable precise quantitative evaluation of the individual samples on a sample plate. The optical scanning of a plurality of samples which have been arranged on a sample plate and subsequently separated chromatography is time-consuming, since the light spot used for illumination of the sample has to be moved successively for each sample over the separation distance assigned to this sample and the light emitted by the sample plate has to be recorded continuously in order subsequently to be able to be evaluated. In addition, the illumination devices used in each case have to be activated in good time between individual measurements with various wavelength ranges and, in the case of UV illumination devices, generally also pre-warmed in order to facilitate the most uniform illumination possible of the sample plate throughout the measurement duration. The optical scanning of a sample plate with 5 to 10 samples therefore usually takes a few minutes and even longer in the case of a change of the illumination. In addition, densitometers of this type are expensive to manufacture and complex during operation.

In order to facilitate rapid and inexpensive evaluation of a sample plate, an image recording of the entire sample plate can be taken using a suitable camera. The image recording taken of the entire sample plate can subsequently be evaluated by suitable evaluation methods. It has been found that a full-plate image recording of this type can be taken very quickly optically and the evaluation with matched software can likewise be carried out rapidly and inexpensively. However, sufficiently homogeneous and constant illumination of the sample plate over a plurality of measurements in order to enable quantitative evaluation of the full-plate image recording is at present only possible with relatively large errors and is very expensive, in particular for illumination with UV light.

It is known from practice to detect the light emitted by the sample plate using a line-by-line optical detector device. For optical scanning of a sample plate, the line-by-line detector device and the sample plate have to be displaced relative to one another. However, all samples arranged alongside one another on the sample plate can be scanned simultaneously using the line-by-line detector device, so that significantly faster image recording can be carried out compared with the commercially available TLC scanners.

In order to carry out such optical scanning of a sample plate, the sample plate can be placed on a commercially available flat-bed scanner with the coated side provided with the samples facing downwards. In order also to facilitate illumination with UV light instead of the usual illumination with visible light and optical scanning of the sample plate, modified flat-bed scanners provided with a UV light source are known from practice. However, it has been found that handling of the sample plate and in particular the placing of the sample plate with the coated side on the glass cover of a flat-bed scanner are problematic and result in contamination. In addition, commercially available scanners are not suitable for UV detection at 254 nm due to the glass plate. The displacement of the illumination device and the line-by-line optical detector device combined therewith does not take place sufficiently uniformly and precisely in the case of the commercially available flat-bed scanners, so that quantitative evaluation of the images recorded using flat-bed scanners of this type are not optimal for reliable quantitative evaluation. In addition, a complete optical scan of a sample plate takes a comparatively long time, in particular in the case of a change in the illumination between two successive image recordings.

It is therefore regarded as an object of the present invention to design a method of the generic type mentioned at the outset for optical scanning of a sample, preferably a chromatographic sample, in such a way that an optical image scan of a sample plate which enables highly reliable quantitative evaluation can be recorded in a short time with the least possible effort. In addition, handling of the sample plate while the measurement operation is carried out should be as user-friendly as possible.

This object is achieved in accordance with the invention in that, in a first measurement step, the sample plate is displaced in a first displacement direction relative to a detector device, illuminated by means of a first illumination device, and a first measurement image of the sample plate is recorded, and in that, in a subsequent second measurement step, the sample plate is displaced in a second displacement direction relative to the detector device, illuminated by means of the second illumination device, and a second measurement image of the sample plate is recorded.

In a preferred embodiment, in a subsequent further displacement direction, which typically corresponds to the first displacement direction, illuminated by means of a third illumination device, and a third measurement image of the sample plate is recorded.

It is equally possible to record further measurement images after the recording of the third measurement image by displacement in further displacement directions and illumination by means of further illumination devices. The successive displacement directions here are preferably in each case opposite.

A measurement image in accordance with the invention is both an image recording, for example an image of a TLC plate on illumination with visible light (wavelength between 370 and 800 nm) or UV light (wavelength less than 370 nm) of various wavelengths or wavelength part-ranges, or a measurement data set, such as, for example, a spectrum recorded using a spectrometer.

The method according to the invention is a method for the optical scanning of a sample, where a sample plate holding the sample is illuminated at least with light from a first illumination device and the light emitted by the sample plate is detected by an optical detector device which reads line by line or field by field, where, in a first measurement step, the sample plate is displaced in a first displacement direction relative to the detector device, illuminated by means of the first illumination device, and a first measurement image of the sample plate is recorded, and, in a subsequent second measurement step, the sample plate is displaced in a second displacement direction relative to the detector device, illuminated by means of the second illumination device, and a second measurement image of the sample plate is recorded. Further measurement steps may optionally be carried out.

The use of a detector device which reads line by line or field by field enables the measurement to be accelerated compared with devices which measure dot by dot. In accordance with the invention, line-by-line scanning means that a plurality of image points lying alongside one another are scanned simultaneously in one direction. In accordance with the invention, field-by-field scanning means that not only a row of image points lying alongside one another is scanned, as is the case for line-by-line scanning, but instead a plurality of rows of these image points lying alongside one another is scanned simultaneously, so that a field of image points is scanned which encompasses two or more image points in each of two directions which are perpendicular to one another. A particularly preferred detector device which reads line by line or field by field is a CCD sensor.

A detector device which is able to record image points lying alongside one another line by line or field by field is also called a line-by-line or field-by-field detector device below.

This type of detection is possible, in particular, since, in accordance with the invention, the illumination devices preferably extend over the entire width of the sample plate to be illuminated. In this way, very homogeneous illumination and illumination strength occurs over the entire width of the sample plate. The illumination devices here can be, for example, tubular light sources or point light sources installed in a row. Homogeneous illumination can preferably additionally be supported by optical components, preferably light-refracting and/or scattering elements, such as diffuser discs or lenses (for example rod lenses). If optical components are used to support homogeneous illumination, the separation of the point light sources can typically be increased. The person skilled in the art is able to select the separation of the point light sources with or without addition of optical components in such a way that sufficiently homogeneous illumination takes place over the entire width of the sample plate.

Furthermore, the illumination devices and the detector device are preferably located above the sample plate, so that the upward-facing side of the sample plate is measured.

In accordance with the invention, two or more illumination devices are employed. 3 illumination devices are preferred. Each illumination device emits in a certain wavelength part-range, i.e. it generates a certain wavelength part-range. These are particularly preferably white-light LEDs for the visible region, UV-LEDs with 366 nm for the UV-A region and mercury vapour lamps for the UV-C region (254 nm).

Examples of alternative illumination devices are LEDs having other wavelengths, halogen lamps or deuterium lamps.

The wavelength part-range of the illumination devices may additionally be restricted by, for example, filters.

For simplification, reference is usually made below to two illumination devices and two measurement steps. The person skilled in the art will also be able to apply the statements made in this respect to devices and methods having three or more measurement steps and correspondingly three or more illumination devices, which also encompassed by the invention.

The recording of two or more measurement images generated by means of two or more different illumination devices enables the evaluation of the measurement images to be combined with one another and the analysis to be improved by the additional information.

If illumination units which require a warm-up time are employed, these are preferably already activated and pre-warmed before their use, i.e., for example, during a prior measurement step.

If, in the case of an illumination device which requires a warm-up time, this illumination device is already activated and is able to pre-warm, preferably in a preparation step, before or while a first measurement image is firstly recorded by means of the first illumination device, a separate warm-up time is not necessary before the recording of the second measurement image by means of the pre-warmed illumination unit. Significantly more homogeneous and uniform illumination of the sample plate can be achieved by means of the already pre-warmed second illumination device during the acquisition of the second measurement image, which improves the reliability and precision of a quantitative evaluation of the second measurement image and thus of the entire quantitative analysis of the sample plate. In addition, the optical scanning of the sample plate can be carried out in a short time, since no or only short waiting times are necessary before commencement of a recording of a first or second measurement image.

During recording of a measurement image, it is not the detector device and the illumination devices that are displaced, but instead the sample plate, which has a significantly lower inherent weight, is moved. The design complexity for rapid and precise displacement of the lightweight sample plate is considerably less than the complexity which would be necessary for comparably precise and rapid displacement of the detector device and the illumination devices. Using a suitably designed drive device for moving the sample plate, it can be achieved that the speed of movement of the sample plate is not limited by the design of the movement device, but instead merely by the maximum possible optical scanning speed of the detector device.

If a plurality of illumination devices, i.e. a plurality of types of light sources, are active during a measurement step, the measurement may be adversely affected, since, during the recording of a measurement image, it is of course only, for example, the luminescence or reflection generated by one illumination device that is to be detected.

In the case of illumination devices which do not require a pre-warming time, such as, for example, LEDs, it is therefore preferred that only one illumination device is active in each case. If this is not appropriate or possible, for example owing to excessively long warm-up times of the illumination device, the influence of the illumination device that is not required in the measurement step must be screened out.

According to an embodiment of the inventive idea, it is proposed that light generated by the second illumination device is screened off from the detector device during the first measurement step. For this purpose, a light-opaque screen may be arranged in the region of the detector device or between the detector device and the second illumination device. The screen can be displaceable in a pivotable or linear manner. If the second illumination device is a UV light source, which is advantageous owing to the pre-warming times that are usually necessary for commercially available UV sources, the detector device may, for example, be covered by a screening device which is opaque to UV light during the recording of the first measurement image and the UV light can thus be kept away from the detector device.

It is preferred in accordance with the invention to screen the light from illumination devices that is not required in a measurement step off from the sample plate and the detector device during this measurement step.

To this end, for example during the first measurement step, the light generated by the second illumination device is not only screened off from the detector device, but also is illuminated exclusively by the first illumination device. In this way, undesired interferences and superimpositions of a first measurement image in, for example, the visible wavelength range which is intended to be generated by illumination with visible light from the first illumination device with the, for example, UV light emitted by the second illumination device and fluorescent light possibly generated thereby in the sample can be prevented. According to a particularly advantageous embodiment of the inventive idea, it is proposed that the second displacement direction is opposite to the first displacement direction and each further displacement direction is in turn opposite to the preceding one. Thus, the sample plate can, for the recording of the first measurement image, be moved in a first direction beneath the detector device and the illumination devices and subsequently moved back again in the opposite direction while the second measurement image is being recorded. In this case, no additional movement paths and no corresponding waiting times are necessary between successive recordings of measurement images.

In a preferred embodiment of the method according to the invention, it is proposed that information from the first measurement image is used for the recording of the second measurement image. In particular, this is information relating to the position of the sample plate, calibration of the lamps or the white balance. The information is preferably processed via corresponding evaluation software.

The invention also relates to a device for the optical scanning of a chromatographic sample having a holder for a sample plate, having a first illumination device and having an optical detector device which reads line by line or field by field.

It is provided in accordance with the invention that the holder has a carrier for the accommodation of the sample plate which can be displaced in a first displacement direction relative to the detector device, that the first illumination device and a second illumination device each preferably extend over a maximum width of a sample plate which can be accommodated in the holder and are each oriented parallel to the line-by-line or field-by-field detector device and perpendicular to the first displacement device, and that the device is preferably designed in such a way that the sample is only illuminated with one wavelength part-range during a recording of a measurement image.

Suitable carriers for the accommodation of the sample plate are, for example, a transport belt which can be moved forwards and backwards, a displaceable carrier plate or preferably a drawer.

A transport belt is able to transport the sample plate rapidly and precisely in one displacement direction and, in a second measurement step, transport it back in the opposite displacement direction.

A drawer into which a sample plate is inserted can be displaced rapidly and precisely with little design complexity. The insertion of a sample plate into a drawer and the subsequent removal of the sample plate after the measurements have been carried out can be designed to be simple and user-friendly. Through suitable positioning aids, such as, for example, spring-actuated clamps, stop elements in the form of ridges or bumps or stop elements which can be displaced in a click-locking manner enable sample plates with different formats, or dimensions to be positioned and fixed reliably within the drawer in a simple manner.

The drawer can be provided with a recess for the accommodation of sample plates or can be designed without a recess. In the case of a drawer without a recess, the sample plate is placed on the flat drawer. If necessary, the drawer has ridges or bumps for the fixing of the sample plate. Sliding of the sample plate or crooked placement of the sample plate can, if necessary, additionally be compensated by suitable image recording software. In accordance with the invention, one or more sample plates can be inserted and measured simultaneously.

Through the design and orientation of the line-by-line or field-by-field detector device and in particular of the first and second illumination device, it can be achieved that the drawer with the sample plate accommodated therein has to be displaced just once over the length of the sample plate perpendicularly to the detector device in order to be able to record a complete measurement image of the sample plate. The illumination devices extending over the entire width of the sample plate enable very uniform and constant illumination of the sample plate to be achieved.

In accordance with the invention, the device is designed in such a way that the sample is only illuminated with one wavelength part-range during a recording of a measurement image in order to enable two different measurement images with complementary information in a short time through a change in the wavelength part-range between two successive measurement images for improved evaluation of the samples located on the sample plate.

For this purpose, it may be provided that the device has a screening device by means of which a wavelength part-range is screened off from the detector device during a recording of a measurement image. The screening can be effected, for example, by light-opaque screening plates or by devices which can optionally be arranged in a region around the detector device so that either only light from the first illumination device or only light from the second illumination device is able to reach the sample plate and enter the detector device. It is likewise conceivable to screen various wavelength part-ranges off from the detector device during successive recordings of measurement images through the use of suitable filter devices.

Alternatively or additionally to this, it is likewise possible, during a recording of a measurement image, to screen off from the sample plate a wavelength part-range of the illumination generated by the first illumination device or by the second illumination device and/or by further illumination devices. In this way, undesired scattered-light effects and luminescence-light effects can also be reduced or completely prevented. The recording of a measurement image is preferably carried out in such a way that only the wavelength part-range generated by one illumination device hits the sample plate. All other active illumination devices are screened off. It is also possible further to restrict the wavelength part-range of the illumination device which illuminates the sample plate in the respective measurement step by means of corresponding filters.

It is likewise conceivable that the detector device has not just one, but instead two or more different optical sensor devices which are sensitive in the same or preferably different or at least partly non-overlapping wavelength part-ranges. In this way, in the case of simultaneous or successive illumination of the sample plate by the first illumination device and by the second illumination device, a first measurement image can be recorded by means of a first sensor device and a second measurement image can be recorded by means of a second sensor device. Examples of sensor devices are CCD sensors (CCD means charge-coupled device), contact image sensors and microspectrometers for the recording of substance spectra. The detector device preferably contains at least one CCD sensor.

One or more optical elements, such as lenses and mirrors, are preferably located between the sensor device of the detector unit, for example the CCD sensor, and the sample plate in order to form the image of the sample plate on the sensor device.

It is preferably provided that the second illumination device, if it requires a warm-up time, has already been activated and is pre-warmed while a first measurement image is firstly recorded by means of the first illumination device, before a second measurement image is recorded by means of the second illumination device.

In a preferred embodiment, it is provided that the light from the illumination devices is preferably directed exclusively at the sample plate. This can take place, for example, by the light sources being employed in a U profile or a box which is only open at the side facing the sample plate. The inside wall of the U profile or box facing the light source may additionally be coated in order to increase the reflections. The advantage of this embodiment is direct orientation of the light at the measurement region without influences of scattered light due to undirected light scattering.

In order to keep optical imaging and measurement errors as low as possible, it is preferably provided that the detector device is arranged less than 100 millimetres, preferably less than 30 millimetres, above the carrier, for example an upper side of the drawer. In the same way, the first illumination device and the second illumination device may also be arranged less than 100 millimetres, preferably less than 30 millimetres, above the carrier, for example the upper side of drawer. This makes a very compact design of the device possible. The upper side of the drawer here means the support surface of the drawer for the sample plate.

Undesired leaking of UV light during a measurement can be prevented very substantially by suitable screening and sealing devices, increasing the operational safety of the device during the performance of measurements.

According to a particularly advantageous embodiment of the inventive idea, it is proposed that the device has a housing in which at least the first illumination device and the second illumination device, the optical detector device and a drive device for the carrier, such as, for example a drawer, are arranged.

It is furthermore preferred that the housing, in the case of a drawer as carrier, has a drawer slot through which the drawer can be at least partly moved out of the housing and moved into the housing. A sample plate can easily be inserted into the drawer which has been at least partly moved out of the housing and can subsequently easily be removed again. The housing can have a very compact design, so that the device can optionally also be designed to be transportable and can be arranged, for example, in a case or box and can thus be transported easily and in a protected manner.

During the performance of a measurement, the first illumination device, the second illumination device, optional further illumination devices and the optical detector device can be screened off from the environment by the housing, so that undesired impairment or falsification of the individual recordings of the measurement images by ambient light or ambient influences can be very substantially excluded. In the same manner, it can also be ensured that, during the performance of a measurement with UV illumination, the UV light generated by the illumination device used for this purpose cannot be unintentionally emitted into the environment.

A suitable sensor device optionally present at or in the drawer slot enables it to be determined whether a sample plate is located in the drawer. In addition, a suitable design of the sensor device also enables the size of the sample plate to be determined, so that the recording and evaluation of the measurement images can be restricted to the dimensions of the sample plate placed in the drawer and the method can thus be accelerated.

The determination of the position of the sample plate is preferably carried out using image analysis software. During acquisition of the first measurement image, which preferably forms through illumination with white light, the image analysis software recognises where the sample plate is located and with what dimensions. In a further step, the sample plate found is straightened virtually with the aid of analysis of the edges of the image. In this way, accurate alignment of the sample plate on placing on the carrier becomes unnecessary. The fact that the sizes of the sample plates are also determined enables the recording and evaluation of the measurement images to be restricted to the dimension of the sample plate inserted. This accelerates the method.

The image analysis software can furthermore preferably carry out an angle correction of sample zones within a sample track. In this way, crooked sample tracks deviating from the flow direction of the eluent can also be scanned as such.

A particularly compact design is facilitated by the housing having an exit slot for the drawer on a housing side opposite the drawer slot. The housing accordingly does not have to be so large that the drawer provided for the accommodation of the sample plate can be stored completely within the housing. Instead, it is possible and, with respect to the smallest, lightest and most transportable measurement instrument possible, advantageous that the housing is matched and restricted to the space requirement of the illumination devices, the optical detector device and the drive device for the drawer. The housing can have a significantly smaller base area than the drawer, which merely has to be pulled in on one side through the drawer slot and transported past the detector device, but can exit again on an opposite side through an exit slot, since it is merely necessary for a strip-shaped or field-shaped region of the sample plate to be illuminated and to be located in a scanning region of the detector device for the acquisition of a measurement image.

The arrangement of the detector device between the first illumination device and the second illumination device enables the achievement of both a very compact design and also uniform illumination and precise detection of the light emitted by the sample plate by means of the detector device.

It is in principle possible for further illumination devices to be arranged alongside or in a region in the vicinity of the detector device in addition to the first illumination device and the second illumination device in order to be able to carry out measurements and record measurement images with three or more different wavelength part-ranges or by means of different methods.

BRIEF DESCRIPTION OF THE DRAWINGS

Illustrative embodiments of the inventive idea are explained in greater detail below and are depicted in the drawing, in which.

Figure 1:
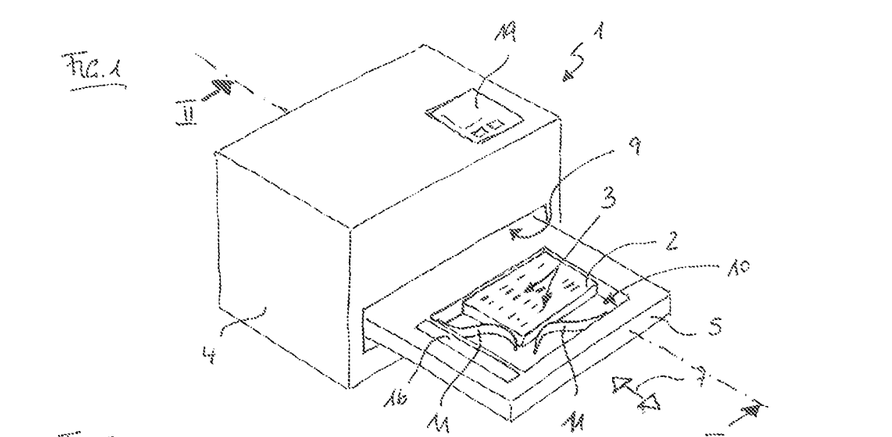
FIG. 1 shows a diagrammatic representation of a device for the optical scanning of a sample plate holding a plurality of samples.
Figure 2:
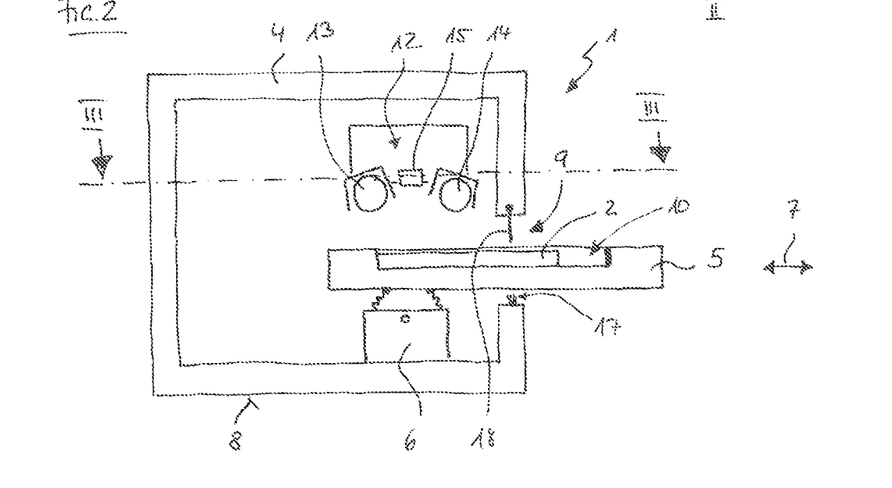
FIG. 2 shows a diagrammatic sectional view of the device shown in FIG. 1 along a section plane II-II in FIG. 1
Figure 3:
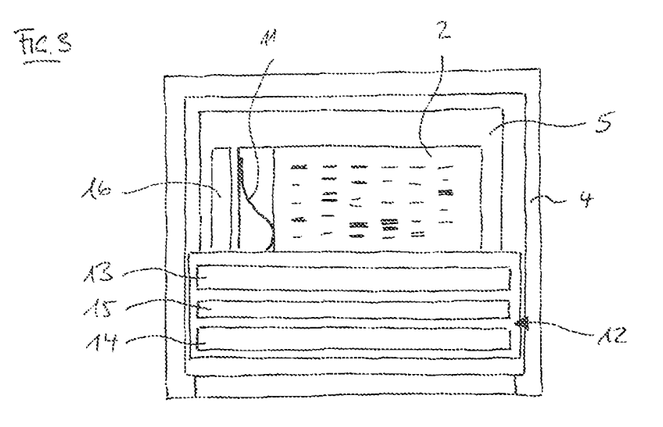
FIG. 3 is a sectional view of the device shown in FIGS. 1 and 2 along a section plane III-III in FIG. 2, where the sample plate has been moved completely into a housing of the device.

A device 1, depicted by way of example in FIGS. 1 to 3, for the optical scanning of a sample plate 2 on which a plurality of chromatographic samples 3 are arranged has a housing 4 and a drawer 5 stored therein in a displaceable manner. The drawer 5 can be moved to and fro along a displacement direction, indicated by an arrow 7, by means of a drive device 6. During this movement, the drawer 5 can be moved partly out of the housing 4 through a drawer slot 9 parallel to a housing base 8 and moved back into the housing 4.

In FIGS. 1 and 2 the drawer 5 is depicted in a state moved completely out or partly out. The drawer 5 has a recess 10, accessible from above, in which the sample plate 2 is located. The sample plate 2 is pushed into a corner of the recess 10 by spring tongues 11 arranged laterally in the recess 10 and thus positioned reliably within the recess 10, which is larger than the sample plate 2 located therein. In this way, it is possible to position the plate formats of, for example, 20×20 centimetres or 20×10 centimetres usually used for thin-layer chromatography in the recess 10 of the drawer 5.

A measurement head 12 is fixed in the housing above the drawer 5. A first illumination device 13, a second illumination device 14 and a line-by-line or field-by-field optical detector device 15 are arranged on an underside of the measurement head 12, facing the drawer 5, in such a way that light emitted by the first illumination device 13 or by the second illumination device 14 illuminates a region of the sample plate 2 located below the measurement head 12 and the light emitted by the sample plate 2 can be detected and recorded by the detector device 15. The first illumination device 13 emits, for example, light in a visible wavelength region. The second illumination device 14 emits, for example, UV light. Both light in the visible wavelength region and also the visible luminescence generated by the excitation with UV light can be detected and recorded by means of the detector device 15 scanning line by line or field by field.

In order to carry out a measurement, firstly the sample plate 2 must be placed in the recess 10 of the drawer 5 and fixed, for example with the aid of the spring tongues 11. Before the beginning of a first recording, the second illumination device 14 is activated and pre-warmed. The second illumination device 14 is covered by means of a cover, which is not depicted in FIGS. 1 to 3, in order to prevent UV light from falling on the sample plate 2 during the pre-warming time and the performance of a first recording. The first illumination device 13 is likewise activated and the drawer 5, which is still moved out of the housing 4, is pulled evenly into the housing 4 and moved past below the detector device 15 in the process. During the pulling-in of the drawer 5, the sample plate 2 arranged in the recess 10 is illuminated with visible light from the first illumination device 13 and the light emitted by the sample plate 2 is detected by the detector device 15. In this way, a first measurement image is recorded.

After the sample plate 2 has been moved completely past the detector device 15, the first illumination device 13 is switched off and the cover is removed from the second illumination device 14, so that the sample plate 2 is no longer illuminated with visible light, but instead with UV light. In order to record the second measurement image, the drawer 5 with the sample plate 2 accommodated therein is again moved in an opposite displacement direction below the detector device 15 scanning line by line or field by field and moved out of the housing 4 through the drawer slot 9 in the process. Since the second illumination device 14 has been pre-warmed during the recording time of the first measurement image, the sample plate 2 is illuminated uniformly by the second illumination device 15 during the recording of the second measurement image.

The first illumination device 13, the second illumination device 14 and the detector device 15 are each designed in strip form or tube form and are arranged, or oriented, in the housing 4 perpendicularly to the displacement direction indicated by means of the arrow 7. The first illumination device 13, the second illumination device 14 and a detector device 15 each extend with their ends or with their detection region respectively beyond the edges of the recess 10 in the drawer 5, so that very homogeneous illumination and illumination strength can be achieved over the entire area of the sample plate 2.

In order to be able to evaluate the individual measurement images as precisely as possible, a reference strip 16, which can likewise be illuminated during a measurement operation and recorded in the measurement image together with the sample plate 2, is optionally installed on the drawer 5 laterally alongside the recess 10.

Instead of a reference strip, the brightness in the regions which do not contain a sample is preferably measured and utilised as reference.

In order to prevent ambient light from entering the housing 4 through the drawer slot 9 during a measurement and affecting the measurement results, and in order to prevent UV light from unintentionally escaping from the housing 4, the drawer slot 9 optionally has a brush strip 17 below the drawer 5 and preferably a screening strip 18 above the drawer 5. The screening strip 18 is mounted in a pivotable manner and at the same time serves as sensor device. If a sample plate 2 has not been placed correctly in the recess 10 of the drawer 5 or if additional objects are located on an upper side of the drawer 5 and the pivotable screening strip 18 is therefore deflected during a displacement of the drawer 5, the measurement operation can be interrupted and, for example, a safety switch-off of the illumination devices 13 and 14 and of the drive can be carried out.

The influences of ambient light can be reduced further by a suitable nature of the inside wall of the housing. The inside of the housing is preferably black, it is particularly preferably black and anodised.

A contact-sensitive display 19 enables simple operation of the device 1 and can at the same time be used to display initial information during performance of a measurement operation.

In a further embodiment, not depicted in the figures, the screening-off of ambient light or UV light does not take place or does not take place only by screening strips or screening brushes, but instead merely or additionally by other screening devices, such as, for example, flaps, curtains, etc.

The two or more illumination devices and the detector device comprising one or more sensor devices are preferably located above the carrier in a fixed, non-movable measurement head 12. The measurement head may furthermore contain screening devices and optical devices, such as mirrors or lenses, which support image acquisition, or also light-refracting and/or light-scattering elements which enable more homogeneous illumination.

Figure 4:
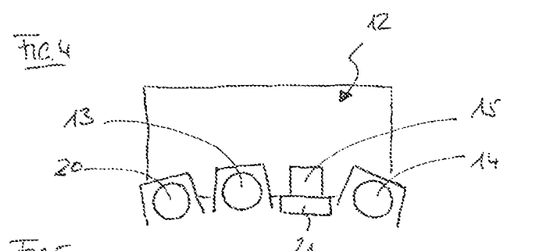
FIG. 4 is a diagrammatic representation of a measurement head of the device having a detector device and having three illumination devices.

Various embodiments of the measurement head 12 are conceivable in order to be able, using the device, to record, as rapidly as possible, various measurement images which can be used together for the evaluation of the chromatographic separations of a sample plate 2. FIG. 4 shows diagrammatically a measurement head 12 in which, in addition to the detector device 15 and the first illumination device 13 and the second illumination device 14, a third illumination device 20 is arranged. The first illumination device 13 emits light in a visible wavelength region. The second illumination device 14 is a mercury vapour lamp, which, through suitable optical elements, emits UVC light having a wavelength of typically 254 nm or a plurality of UV LEDs arranged in strip form. The third illumination device 20 has a number of light-emitting diodes arranged in strip form or a mercury vapour lamp, which likewise, in combination with suitable optical components, emits light having a wavelength of typically 366 nm and having a very homogeneous illumination strength.

In order to prevent UV light from the second illumination device 14 being collected and acquired by the detector device 15 during the pre-warming time of the second illumination device 14 and the simultaneous recording of a first measurement image, a screening device 21 which is opaque to UV light may screen off the detector device 15 during the first measurement operation. The first illumination device 13, which emits visible light, and the third illumination device 20, consisting, for example, of LEDs, do not require a pre-warming time and can each be activated for the duration of the measurement operation in question and subsequently switched off again.

Figure 5:
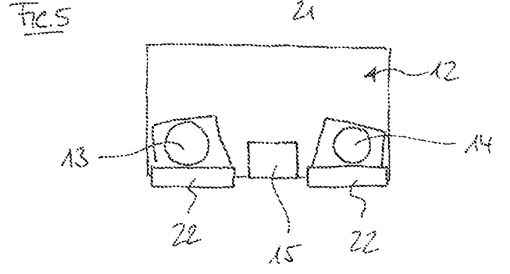
FIG. 5 is a diagrammatic representation of a different design of a measurement head of the device having one detector device and having two illumination devices.

In the variant depicted in FIG. 5, the measurement head 12 has in each case a displaceable screening device 22 in front of the first illumination device 13 and in front of the second illumination device 14, by means of which the illumination device 13, 14 in question can be screened or uncovered.

Using the device 1 according to the invention, measurements of chromatographic sample plates 2 can be carried out very rapidly. However, other measurements are also possible with the device 1, for example quality tests, particle analyses or detection of security pigments. Further chemical or biological evaluations, for example of gels, agar plates, test sticks, etc., are also possible. In accordance with the invention, sample plates are therefore all samples which can be accommodated by a carrier of a device according to the invention, such as thin-layer chromatography plates, gels, agar plates, test sticks, printed circuit boards, etched circuit boards, tissue sections, samples of paper, plastic, metal, minerals, granules. The sample plate is preferably a thin-layer chromatography plate. In accordance with the invention, the carrier is able to accommodate one or more sample plates.

The carrier, for example in the form of a drawer 5, can also be removed completely from the housing 4 and re-used for carrying out measurements. Thus, for example, the sample plate 2 may already be arranged in the drawer before or during the chromatographic separation of the samples arranged thereon and thus stored and transported in a protected manner during preparatory or subsequent method steps.

Even without further comments, it is assumed that a person skilled in the art will be able to utilise the above description in the broadest scope. The preferred embodiments and examples should therefore merely be regarded as descriptive disclosure which is absolutely not limiting in any way.

The complete disclosure content of all applications, patents and publications mentioned above and below, in particular the corresponding applications EP 14004313.4, filed on 19 Dec. 2014, and EP 15000889.4, filed on 26 Mar. 2015, is incorporated into this application by way of reference.

The invention claimed is:

1. A method for the optical scanning of a sample (3), where a sample plate (2) holding the sample (3) is, in a first measurement step, illuminated at least with light from a first illumination device (13) and the light emitted by the sample plate (2) is detected by an optical detector device (15) which reads line by line or field by field and a first measurement image of the sample plate (2) is recorded, where the sample plate (2) is displaced in a first displacement direction relative to the detector device (15), and where, in a subsequent second measurement step, the sample plate (2) is displaced in a second displacement direction relative to the detector device (15), illuminated by a second illumination device (14) and a second measurement image of the sample plate (2) is recorded, wherein the illumination devices (13, 14) and the detector device (15) are located above the sample plate (2) and the illumination devices (13, 14) extend over the entire width of the sample plate to be illuminated.

2. The method according to claim 1, wherein in a subsequent third measurement step, the sample plate (2) is displaced in a third displacement direction relative to the detector device (15), illuminated by a third illumination device (20) and a third measurement image of the sample plate (2) is recorded.

3. The method according to claim 1, wherein the second illumination device (14) and/or third illumination device is activated in a preparation step before and/or during a preceding measurement step.

4. The method according to claim 1, wherein light generated by the second illumination device (14) is screened off from the sample plate (2) during the first measurement step.

5. The method according to claim 1, wherein the second displacement direction is opposite to the first displacement direction.

6. The method according to claim 1, wherein information from the first measurement image is used for the recording of the second measurement image.

7. A method for the optical scanning of a sample (3), where a sample plate (2) holding the sample (3) is, in a first measurement step, illuminated at least with light from a first illumination device (13) and the light emitted by the sample plate (2) is detected by an optical detector device (15) which reads line by line or field by field and a first measurement image of the sample plate (2) is recorded, where the sample plate (2) is displaced in a first displacement direction relative to the detector device (15), and where, in a subsequent second measurement step, the sample plate (2) is displaced in a second displacement direction relative to the detector device (15), illuminated by the second illumination device (14) and a second measurement image of the sample plate (2) is recorded, wherein the illumination devices (13, 14) and the detector device (15) are located above the sample plate and the illumination devices (13, 14) extend over the entire width of the sample plate to be illuminated, and wherein the illumination devices (13, 14) and the detector device (15) are fixed so that they are non-movable.

8. The method according to claim 7, wherein in a subsequent third measurement step, the sample plate (2) is displaced in a third displacement direction relative to the detector device (15), illuminated by a third illumination device (20) and a third measurement image of the sample plate (2) is recorded.

9. The method according to claim 7, wherein the second illumination device (14) and/or third illumination device is activated in a preparation step before and/or during a preceding measurement step.

10. The method according to claim 7, wherein light generated by the second illumination device (14) is screened off from the sample plate (2) during the first measurement step.

11. The method according to claim 1, wherein the sample plate (2) is made of a metal foil.

12. The method according to claim 7, wherein information from the first measurement image is used for the recording of the second measurement image, which information optionally relates to the position of the sample plate, calibration of the lamps or the white balance.

13. A device (1) for the optical scanning of a chromatographic sample (3) having a holder for a sample plate (2) having a first illumination device (13) and having an optical detector device (15), wherein the detector device (15) reads line by line or field by field, the holder has a carrier (5) for the accommodation of the sample plate (2) which can be displaced in a first displacement direction relative to the detector device (15), and the first illumination device (13) and a second illumination device (14) each extend over a maximum width of a sample plate (2) which can be accommodated in the holder and are each orientated parallel to the line-by-line or field-by-field detector device (15) and perpendicular to the first displacement direction, wherein the illumination devices (13, 14) and the detector device (15) are located above the sample plate (2) and the illumination devices (13, 14) extend over the entire width of the sample plate to be illuminated.

14. The device (1) according to claim 13, wherein the carrier is a drawer (5).

15. The device (1) according to claim 14, wherein the device (1) has a housing (4) in which the first illumination device (13) and the second illumination device (14), the optical detector device (15) and the drive device (6) for the drawer (5) are arranged, and the housing (4) has a drawer slot (9) through which the drawer (5) can be partly moved out of the housing (4) and can be moved into the housing (4).

16. The device (1) according to claim 15, wherein the drawer slot (9) has a sensor device for detecting a sample plate (2).

17. The device (1) according to claim 15, wherein the housing (4) has an exit slot for the drawer (5) on a housing side opposite the drawer slot (9).

18. The device (1) according to claim 13, wherein a wavelength part-range is screened off from the sample plate (2) during a recording of a measurement image.

19. The device (1) according to claim 13, wherein the detector device (15) is arranged less than 100 mm above the carrier (5).

20. The device (1) according to claim 13, wherein the detector device (15) is arranged between the first illumination device (13) and the second illumination device (14).

* * * * *